(12) United States Patent
Sigmon, Jr.

(10) Patent No.: US 9,408,662 B2
(45) Date of Patent: Aug. 9, 2016

(54) SPHINCTEROTOME HAVING EXPANDABLE TINES

(75) Inventor: John Crowder Sigmon, Jr., Greensboro, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1065 days.

(21) Appl. No.: 13/465,622

(22) Filed: May 7, 2012

(65) Prior Publication Data
US 2013/0296855 A1 Nov. 7, 2013

(51) Int. Cl.
*A61B 18/14* (2006.01)
*A61B 18/00* (2006.01)
*A61B 17/00* (2006.01)

(52) U.S. Cl.
CPC ... *A61B 18/1492* (2013.01); *A61B 2017/00455* (2013.01); *A61B 2018/00083* (2013.01); *A61B 2018/00107* (2013.01); *A61B 2018/00267* (2013.01); *A61B 2018/00553* (2013.01); *A61B 2018/00595* (2013.01); *A61B 2018/00601* (2013.01); *A61B 2018/144* (2013.01); *A61B 2018/1497* (2013.01)

(58) Field of Classification Search
CPC combination set(s) only.
See application file for complete search history.

(56) References Cited

U.S. PATENT DOCUMENTS

| | | | |
|---|---|---|---|
| 4,228,802 A | 10/1980 | Trott | |
| 5,100,423 A | 3/1992 | Fearnot | |
| 5,201,732 A | 4/1993 | Parins | |
| 5,505,730 A | 4/1996 | Edwards | |
| 5,558,672 A | 9/1996 | Edwards et al. | |
| 5,569,241 A | 10/1996 | Edwards | |
| 5,681,308 A | 10/1997 | Edwards et al. | |
| 5,746,224 A | 5/1998 | Edwards | |
| 5,769,846 A | 6/1998 | Edwards et al. | |
| 5,800,429 A | 9/1998 | Edwards | |
| 5,814,064 A | 9/1998 | Daniel et al. | |
| 5,823,197 A | 10/1998 | Edwards | |
| 5,827,273 A | 10/1998 | Edwards | |
| 5,827,277 A | 10/1998 | Edwards | |
| 5,843,077 A | 12/1998 | Edwards | |
| 5,885,258 A | 3/1999 | Sachdeva et al. | |
| 5,899,917 A | 5/1999 | Edwards et al. | |
| 5,911,739 A | 6/1999 | Kordis | |
| 5,964,755 A | 10/1999 | Edwards | |
| 6,002,968 A | 12/1999 | Edwards | |
| 6,006,755 A | 12/1999 | Edwards | |
| 6,009,877 A | 1/2000 | Edwards | |
| 6,024,743 A | 2/2000 | Edwards | |
| 6,033,397 A | 3/2000 | Laufer et al. | |
| 6,033,401 A | 3/2000 | Edwards et al. | |
| 6,036,689 A | 3/2000 | Tu et al. | |

(Continued)

OTHER PUBLICATIONS

International Search Report and Written Opinion for PCT/US2013/039883 dated Aug. 8, 2013, 14 pages.

*Primary Examiner* — Amanda Patton
(74) *Attorney, Agent, or Firm* — Brinks Gilson & Lione (57) ABSTRACT

A sphincterotome includes a plurality of tines that are longitudinally disposed at a distal end of the sphincterotome. One of the tines is configured as a cutting wire of the sphincterotome and is electrically coupled to an electrical source. The other tines are configured as stabilizing wires to stabilize the cutting wire in a cutting position. In addition, the other tines are electrically insulated from the cutting wire and the electrical source. The plurality of tines are movable between an expanded and a non-expanded configuration. Electrocautery is performed when the tines are in the expanded configuration.

15 Claims, 7 Drawing Sheets

(56) References Cited

U.S. PATENT DOCUMENTS

| | | |
|---|---|---|
| 6,039,757 A | 3/2000 | Edwards et al. |
| 6,044,846 A | 4/2000 | Edwards |
| 6,051,008 A | 4/2000 | Saadat |
| 6,056,744 A | 5/2000 | Edwards |
| 6,092,528 A | 7/2000 | Edwards |
| 6,149,647 A | 11/2000 | Tu |
| 6,254,598 B1 | 7/2001 | Edwards et al. |
| 6,258,087 B1 | 7/2001 | Edwards et al. |
| 6,273,886 B1 | 8/2001 | Edwards et al. |
| 6,315,776 B1 | 11/2001 | Edwards et al. |
| 6,325,798 B1 | 12/2001 | Edwards et al. |
| 6,355,031 B1 | 3/2002 | Edwards et al. |
| 6,358,245 B1 | 3/2002 | Edwards et al. |
| 6,375,668 B1 | 4/2002 | Gifford et al. |
| 6,402,744 B2 | 6/2002 | Edwards et al. |
| 6,405,732 B1 | 6/2002 | Edwards et al. |
| 6,440,128 B1 | 8/2002 | Edwards et al. |
| 6,464,689 B1 | 10/2002 | Qin et al. |
| 6,464,697 B1 | 10/2002 | Edwards et al. |
| 6,517,535 B2 | 2/2003 | Edwards |
| 6,551,310 B1 | 4/2003 | Ganz et al. |
| 6,562,034 B2 | 5/2003 | Edwards et al. |
| 6,616,678 B2 | 9/2003 | Nishtala et al. |
| 6,645,201 B1 | 11/2003 | Utley et al. |
| 6,673,070 B2 | 1/2004 | Edwards et al. |
| 6,712,074 B2 | 3/2004 | Edwards et al. |
| 6,712,814 B2 | 3/2004 | Edwards et al. |
| 6,783,523 B2 | 8/2004 | Qin et al. |
| 6,790,207 B2 | 9/2004 | Utley et al. |
| 6,802,841 B2 | 10/2004 | Utley et al. |
| 6,872,206 B2 | 3/2005 | Edwards et al. |
| 6,974,456 B2 | 12/2005 | Edwards et al. |
| 6,994,704 B2 | 2/2006 | Qin et al. |
| 7,056,320 B2 | 6/2006 | Utley et al. |
| 7,122,031 B2 | 10/2006 | Edwards et al. |
| 7,125,407 B2 | 10/2006 | Edwards et al. |
| 7,150,745 B2 | 12/2006 | Stern et al. |
| 7,165,551 B2 | 1/2007 | Edwards et al. |
| 7,198,635 B2 | 4/2007 | Danek et al. |
| 7,276,061 B2 | 10/2007 | Schaer et al. |
| 7,293,563 B2 | 11/2007 | Utley et al. |
| 7,329,254 B2 | 2/2008 | West et al. |
| 7,344,535 B2 | 3/2008 | Stern et al. |
| 7,458,378 B2 | 12/2008 | Utley et al. |
| 7,468,060 B2 | 12/2008 | Utley et al. |
| 7,507,234 B2 | 3/2009 | Utley et al. |
| 7,507,238 B2 | 3/2009 | Edwards et al. |
| 7,530,979 B2 | 5/2009 | Ganz et al. |
| 7,556,628 B2 | 7/2009 | Utley et al. |
| 7,585,296 B2 | 9/2009 | Edwards et al. |
| 7,632,268 B2 | 12/2009 | Edwards et al. |
| 7,648,500 B2 | 1/2010 | Edwards et al. |
| 7,670,347 B2 | 3/2010 | Kessler et al. |
| 7,699,844 B2 | 4/2010 | Utley et al. |
| 7,776,062 B2 | 8/2010 | Besselink et al. |
| 7,837,693 B2 | 11/2010 | Cheng et al. |
| 7,850,685 B2 | 12/2010 | Kunis et al. |
| 7,857,808 B2 | 12/2010 | Oral et al. |
| 7,922,715 B2 | 4/2011 | Qin et al. |
| 7,938,826 B2 | 5/2011 | Davis et al. |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,152,803 B2 | 4/2012 | Edwards et al. |
| 2003/0032953 A1* | 2/2003 | VanDusseldorp ........ A61B 1/32 606/41 |
| 2004/0153056 A1 | 8/2004 | Muller et al. |
| 2006/0247618 A1 | 11/2006 | Kaplan et al. |
| 2007/0129753 A1 | 6/2007 | Quinn et al. |
| 2009/0005778 A1 | 1/2009 | Ducharme |

* cited by examiner

SPHINCTEROTOME HAVING EXPANDABLE TINES

TECHNICAL FIELD

The present invention relates generally to medical devices, and more particularly to sphincterotomes.

BACKGROUND

A sphincterotome is a medical device that is used to perform a sphincterotomy, a medical procedure in which a sphincter muscle, such as the sphincter of Oddi, is cut. By cutting the sphincter muscle, the constrictive nature of the muscle is relieved, which allows other medical devices to pass through the sphincter muscle and into another area of the patient to perform various medical procedures. For example, when the sphinter of Oddi is cut, medical devices may pass through the duodenal papilla and enter into the biliary tree and perform one or more medical procedures, such as removal of bile duct stones from the biliary tree.

The sphincterotome includes a cutting wire that is used to cut the sphincter muscle. When the sphincter muscle is cut using the cutting wire, the constrictive nature of the sphincter muscle is relieved. However, some tension around the sphincter muscle still exists, which may cause the distribution of the tension around the sphincter muscle to be uneven or change as the muscle is being cut. The uneven distribution of tension may cause instability in the position of the cutting wire. For example, while cutting, the uneven distribution of tension may force the cutting wire away from a desired cutting position.

BRIEF SUMMARY

The present disclosure describes a sphincterotome that includes a plurality of tines that are longitudinally disposed at a distal portion of the sphincterotome. The plurality of tines are movable between an expanded configuration and a non-expanded configuration. One of the tines is configured as a cutting wire and is electrically coupled to an electrical source. The other tines are configured as stabilizing wires and are electrically insulated from cutting wire.

The present disclosure also describes a method of operating a sphincterotome. The method includes configuring a plurality of tines longitudinally disposed at a distal end of the sphincterotome to a non-expanded configuration. The method also includes moving the distal end within an opening of a sphincter muscle and moving the plurality of tines to an expanded configuration to widen the opening of the sphincter muscle. Further, the method includes transmitting an electrical signal to one of the plurality of tines to perform electrocautery on the sphincter muscle using the one of the plurality of tines.

DETAILED DESCRIPTION

Figure 1:
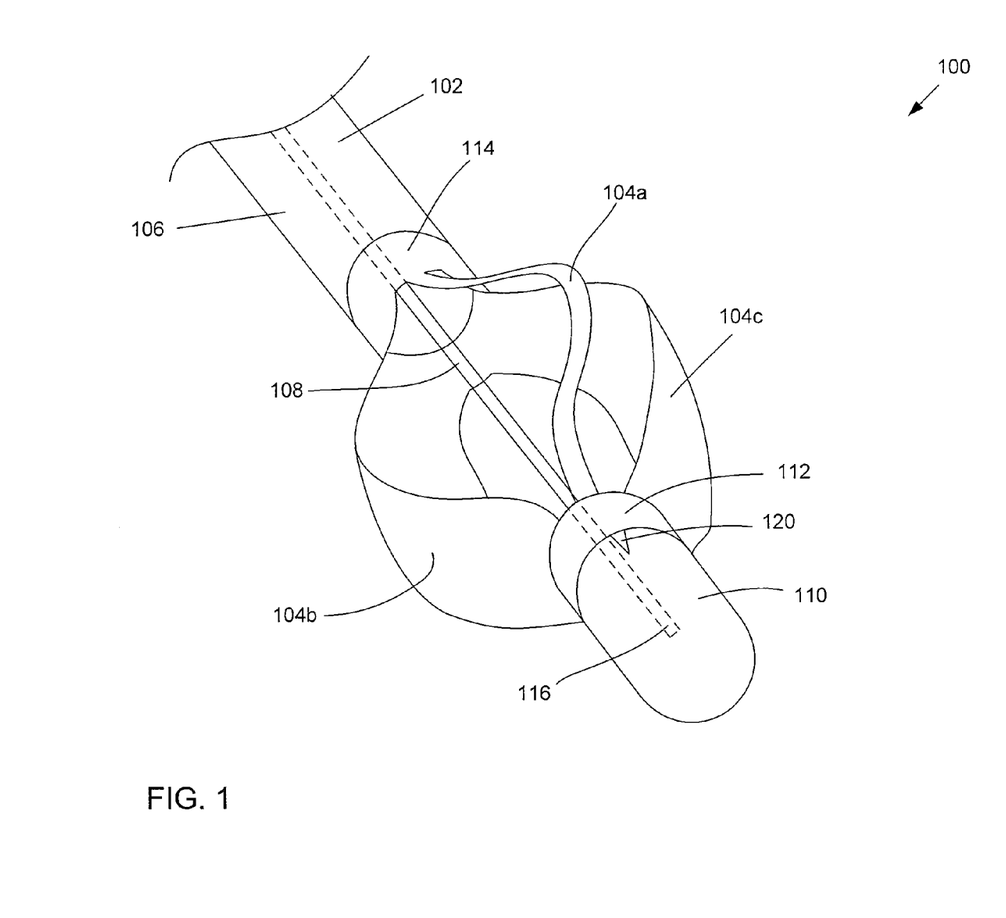
FIG. 1 shows a perspective view of a distal portion of an example sphincterotome having a plurality tines longitudinally disposed tines.

FIG. 1 shows a perspective view of a distal portion 102 of an example sphincterotome 100. The sphincterotome 100 has a plurality of tines 104 that are movable between an expanded configuration and a non-expanded configuration. FIG. 1 shows the tines 104 in the expanded configuration. In the expanded configuration, the tines 104 radially extend from an elongate tubular member or cannula 106 of the sphincterotome 100. One of the tines 104a is configured as a cutting wire that is used to cut a sphincter muscle at a treatment site. The cutting wire 104a is configured to be electrically coupled to an electrical source (shown in FIG. 7), which provides an electrical signal, such as electric current, to the cutting wire 104a. By being electrically coupled to the electrical source, electrocautery may be performed using the cutting wire 104a to cut the sphincter muscle. The other of the tines 104b, 104c may be configured as stabilizing wires that may stabilize the cutting wire 104a in a cutting position when electrocautery is being performed. The other of the tines 104b, 104c may also be configured as support wires that support the sphincter muscle as the opening of the sphincter muscle is widened while the cutting wire 104a is cutting the sphincter muscle. The cutting wire may be configured as a monopolar device, which uses a grounding pad under a patient when electrocautery is being performed. The other tines 104b, 104c may be electrically insulated from cutting wire 104a as well as the electrical source. In some example configurations, a shrink tube and/or a parylene coating may be applied to the other tines 104b, 104c to electrically insulate them from the cutting wire 104a. Other insulating materials may be used in alternative configurations. The sphincterotome 100 may also include an indicator 120 that provides a visual indication as to which of the tines 104 is the cutting wire. The indicator 120 may include any variety of shapes or patterns, such as an arrow or triangle shown in FIG. 1. In addition, the indicator may be positioned at a distal end 110 of the sphincterotome 100 and in axial alignment with the cutting wire 104a, although other locations on the sphincterotome 100 may be used. In alternative configurations, the sphincterotome 100 may not include the indicator 120 and the tine that is the cutting wire 104a may be readily identifiable because it has a width or circumferential length that is less or substantially less than the other wires 104b, 104c configured as stabilizing wires. In addition or alternatively, the cutting wire 104a may be identified by having a different color than the stabilizing wires 104b, 104c. Various configurations or combinations of configurations are possible.

The sphincterotome 100 may further include a stylet that is longitudinally disposed within the tubular member 106. The stylet 108 may extend from a proximal end (shown in FIG. 7) to the distal end 110 the tubular member 106 of the sphincterotome 100. The stylet 108 may be configured to axially move relative to the tubular member 106. In addition, the stylet 108 may be operatively coupled to the tines 104. Through axial movement, the stylet 108 may be configured to move the tines 104 between the expanded configuration and the non-expanded configuration. To move the tines 104 between the expanded configuration and the non-expanded configuration, the stylet 108 may be operatively coupled to a first end of the tines 104 and be configured to axially move relative to a second end of the tines 104. Axial movement of the stylet 108 may axially move the first end of the tines 104 relative to the second end of the tines 104, causing the tines to move between the expanded configuration and the non-expanded configuration.

In one configuration, as shown in FIG. 1, the first end may be a distal end 112 of the tines 104 and the second end may be a proximal end 114 of the tines 104. Through axial movement, the stylet 108 may be configured to move the distal end 112 relative to the proximal end 114. When the stylet 108 axially moves in a proximal direction, the stylet 108 may move the distal end 112 of the tines 104 proximally toward the proximal end 114, causing the tines 104 to move to the expanded configuration. Also, when the stylet 108 axially moves in a distal direction, the stylet 108 may move the distal end 112 of the tines 104 distally away from the proximal end 114, causing the tines 104 to move to the non-expanded configuration. In alternative configurations, the first end may be the proximal end 114 and the second end may be the distal end 112, and the stylet 108 may be configured to be operatively coupled to the proximal end 114 so that the stylet 108 moves the proximal end 114 relative to the distal end 112. In addition, alternative embodiments may include one or more devices other than the stylet 108 configured to be operatively coupled to the tines 104 to move the tines between the expanded and the non-expanded configurations. For example, a wire external to the tubular member 106 of the sphincterotome may be couple and/or connected to the tines, causing the ends 112, 114 of the tines 104 to move toward and away from each other.

In the sphincterotome 100 shown in FIG. 1, the stylet 108 may be operatively coupled to the distal end 112 of the tines 104 by having a distal end 116 that is fixedly attached and/or connected to the distal end 110 of the tubular member 106 of the sphincterotome 100. As explained in more detail below, the distal end 116 of the stylet 108 may be fixedly attached to an inner portion of the distal end 118 of the tubular member 106. In turn, the distal end 118 of the tubular member 106 may be connected to the distal end 112 of the tines 104.

Figure 2:
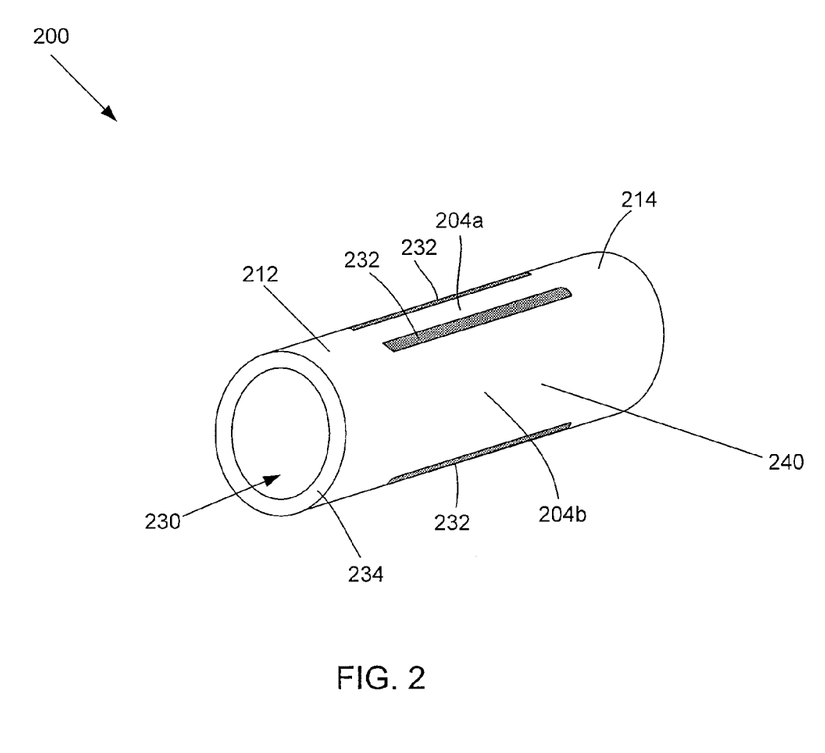
FIG. 2 shows a perspective view of an example expandable basket.

FIG. 2 shows a perspective view of a configuration of the tines 104, in which the tines 104 are configured as an expandable basket 200. The expandable basket 200 comprises an elongate tubular member 202 having a central lumen 230 extending from a first end 212 of the tubular member 202 to a second end 214 of the tubular member 202. The first end 212 and the second end 214 may correspond to first and second ends 112, 114 shown in FIG. 1. The tubular member 202 may also include a middle portion 240 disposed in between and connected to the first and second ends 212, 214. The middle portion may include tines 204, which may correspond to tines 104 shown in FIG. 1. The tines may be configured to have a predetermined longitudinal length. In one example, the longitudinal length may be approximately one inch and/or in a range of about four tenths (0.4) inches to two inches. Other longitudinal lengths may be used for the tines 204. The tines 204 may be defined and/or formed by longitudinal slots or gaps 232 formed and/or disposed in a wall 234 of the tubular member 202. The slots 232 may extend through the wall 234, from an outer surface to an inner surface of the wall 234. In addition, the slots 232 may longitudinally extend in the middle portion 240 from a position before the first end 212 to the second end 214. The slots 232 may be configured so that the tines 204 are physically separate elements that may radially move independent of each other in the middle portion. However, because the slots 232 do not extend to the first and second ends 212, 214, the tines 204 are connected at the ends 212, 214 and may move axially together at the respective ends 212, 214. In contrast to FIG. 1, the tines 204 are shown in the non-expanded configuration.

The expandable basket 200 may be made of an electrically conductive material, such as nitinol. The nitinol expandable basket 200 may be preformed as a nitinol cannula. When the expandable basket 200 is unbiased, the tines 204 are configured in the straightened, non-expanded configuration. The tines configured as stabilizing wires may be electrically insulated from the tine configured as a cutting wire by applying a shrink tube or parylene coating to the stabilizing wires. As such, although electricity may flow through the stabilizing wires, the current will be insulated from outer surfaces of the stabilizing wires.

Figure 3:
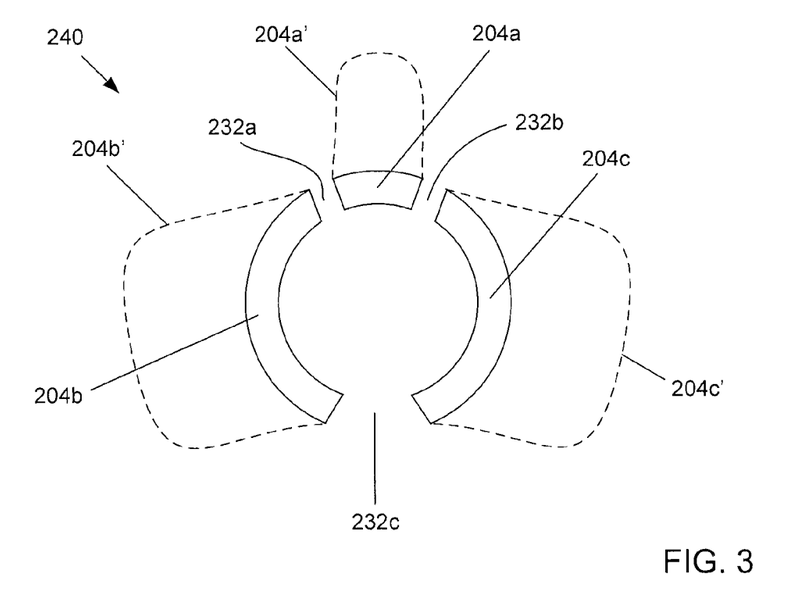
FIG. 3 shows a cross-sectional axial view of a middle portion of the example expandable basket having three tines.

FIG. 3 shows a cross-sectional view of the middle portion 240 when viewed along a longitudinal axis of the expandable basket 200. The cross section view of FIG. 3 shows three tines 204a, 204b, 204c. One of the tines 204a is configured as a cutting wire of the sphincterotome and the other tines 204a, 204b are configured as stabilizing wires that are configured to stabilize the cutting wire 204a when the cutting wire 204a is positioned to cut the sphincter muscle. As shown in FIG. 3, three slots or gaps 232 extend through the wall 234 to form and/or define the tines 204. The slots 232 are positioned in the wall 234 so that the tines 204 each have a predetermined circumferential length. In one example configuration, the slots 232 are positioned so that the circumferential length of the tine 204a configured as the cutting wire is less than the circumferential lengths of the other tines 204b, 204c configured as the stabilizing wires. In one example the circumferential length of the cutting wire is approximately ten one-thousandths (0.010) of an inch. In alternative configurations, the circumferential lengths of the tines 204a, 204b, and 204c are equal or substantially equal. In yet other alternative configurations, the circumferential length of the cutting wire 204a may be greater than one or more of the other tines 204b, 204c that are configured as the stabilizing wires. In addition, the slots 232a, 232b, and 232c may have the same, substantially the same, or different circumferential lengths. For example, as shown in FIG. 3, slots 232a and 232b have the same circumferential length, and are different and/or less than the circumferential length of the slot 232c. Various configurations are possible.

FIG. 3 shows a cross-sectional profile of the tines 204a, 204b, 204c in the non-expanded configuration, as denoted by solid lines. FIG. 3 also shows a cross-sectional profile of the tines 204a', 204b' 204c' in the expanded configuration, as denoted by dashed lines. In the expanded configuration, the tines 204 generally move in a radial direction that is in alignment with a midpoint of the respective tine.

Figure 4:
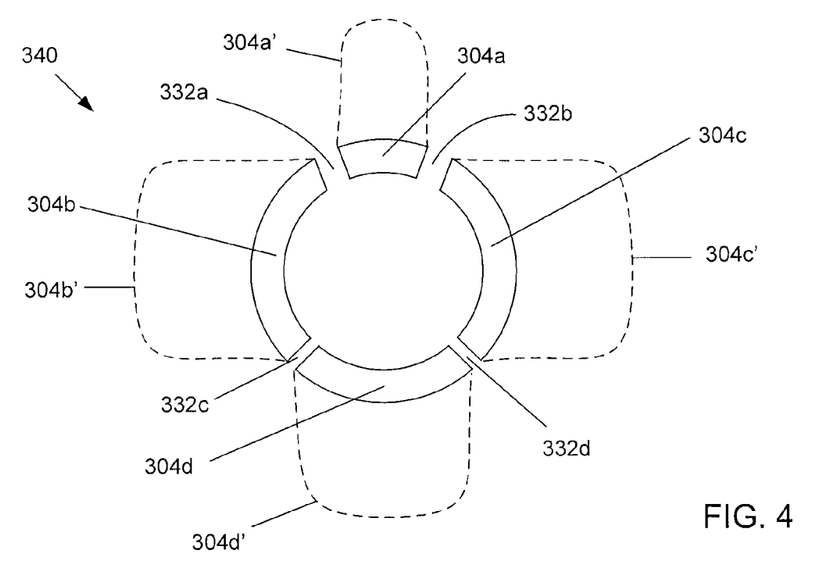
FIG. 4 shows a cross-sectional axial view of a middle portion of an alternative example expandable basket having four tines.

FIG. 4 shows a cross-sectional profile of a middle portion 340 of an alternative configuration of an expandable basket 300 that has four tines 304a, 304b, 304c, 304d. Like tines 204, one of the tines 304a of the expandable basket 300 is configured as a cutting wire and the other of the tines 304b, 304c, 304d are configured as stabilizing wires that stabilize the cutting wire 304a in a cutting position. Also, like tines 204, the tine 304a configured as the cutting wire may have a circumferential length that is less than circumferential lengths of the other tines 304b, 304c, 304d that are configured as stabilizing wires. To define and/or form the four tines 304a, 304b, 304c, 304d, four slots or gaps 332 extend through a wall 334 of the expandable basket 300. The circumferential lengths of the slots 332 may vary and/or may be configured to be the same, substantially the same, or different from each other. For example, slots 332a and 332b forming the cutting wire 304a may be configured to have the same circumferential length, which may different than the circumferential length of slot 332c and/or slot 332d. Similarly, slots 332c and slot 332d may have the same circumferential length, which may be different than the circumferential length of slot 332a and/or slot 332b. Various configurations are possible.

Also, FIG. 4 shows a cross-sectional profile of the tines 304a, 304b, 304c, 304d in the non-expanded configuration, as denoted by solid lines. FIG. 4 also shows a cross-sectional profile of the tines 304a', 304b', 304c', 304d' in the expanded configuration, as denoted by dashed lines. In the expanded configuration, the tines 304 generally move in a radial direction that is in alignment with a midpoint of the respective tine.

FIGS. 1-4 show expandable basket configurations having three or four tines. Other expandable basket configurations may include two tines or more than four tines, where one of the tines is configured as a cutting wire to cut the sphincter muscle and the other of the tines are configured as stabilizing wires that stabilize the cutting wire in a cutting position.

Figure 5:
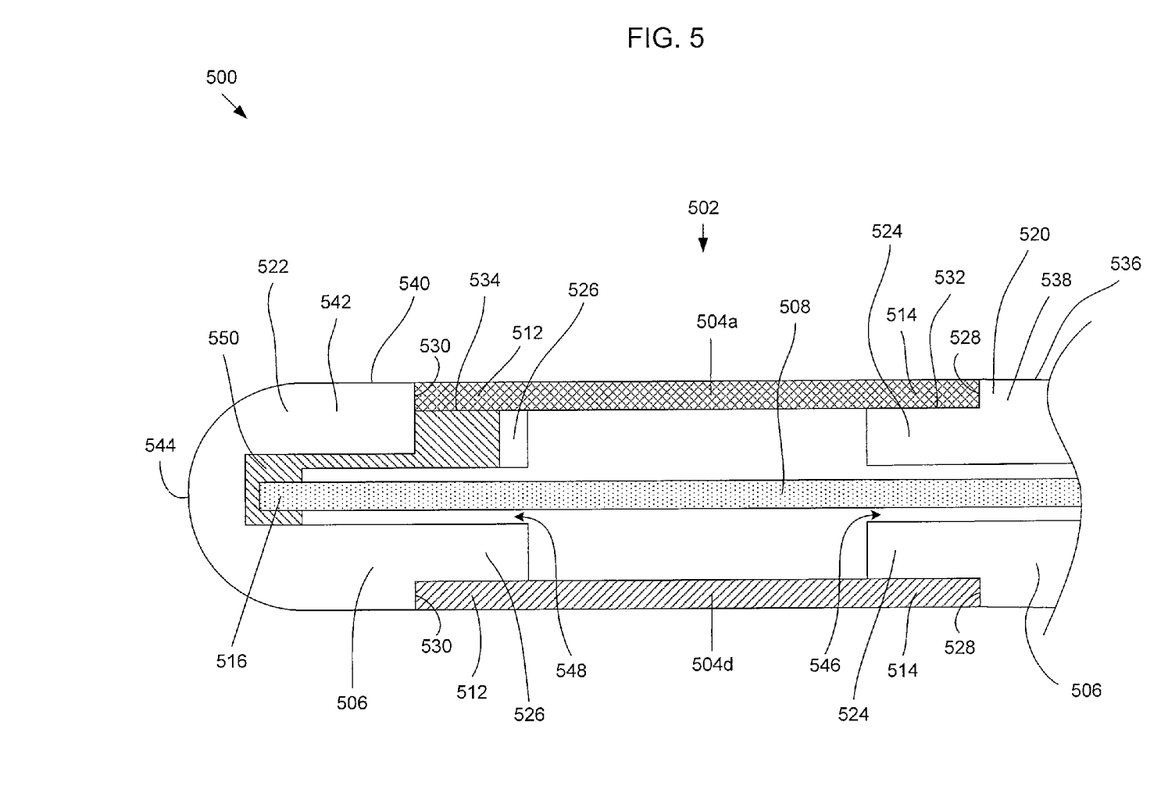
FIG. 5 shows a cross-sectional side view of a distal portion of an example sphincterotome having a plurality of longitudinally disposed tines, where the tines are configured in a non-expanded configuration.

FIG. 5 shows a cross-sectional side view of a distal portion 502 of a sphincterotome 500 having tines 504 that are movable between a non-expandable configuration and an expandable configuration. FIG. 5 shows the tines 504 in the non-expandable configuration. In the non-expandable configuration, the tines 504 may be in a straightened or substantially straightened configuration. Also, in the non-expandable configuration, the tines 504 may be in an unbiased configuration as the tines 504 are not being axially biased by a tubular member 506 of the catheter.

Figure 7:
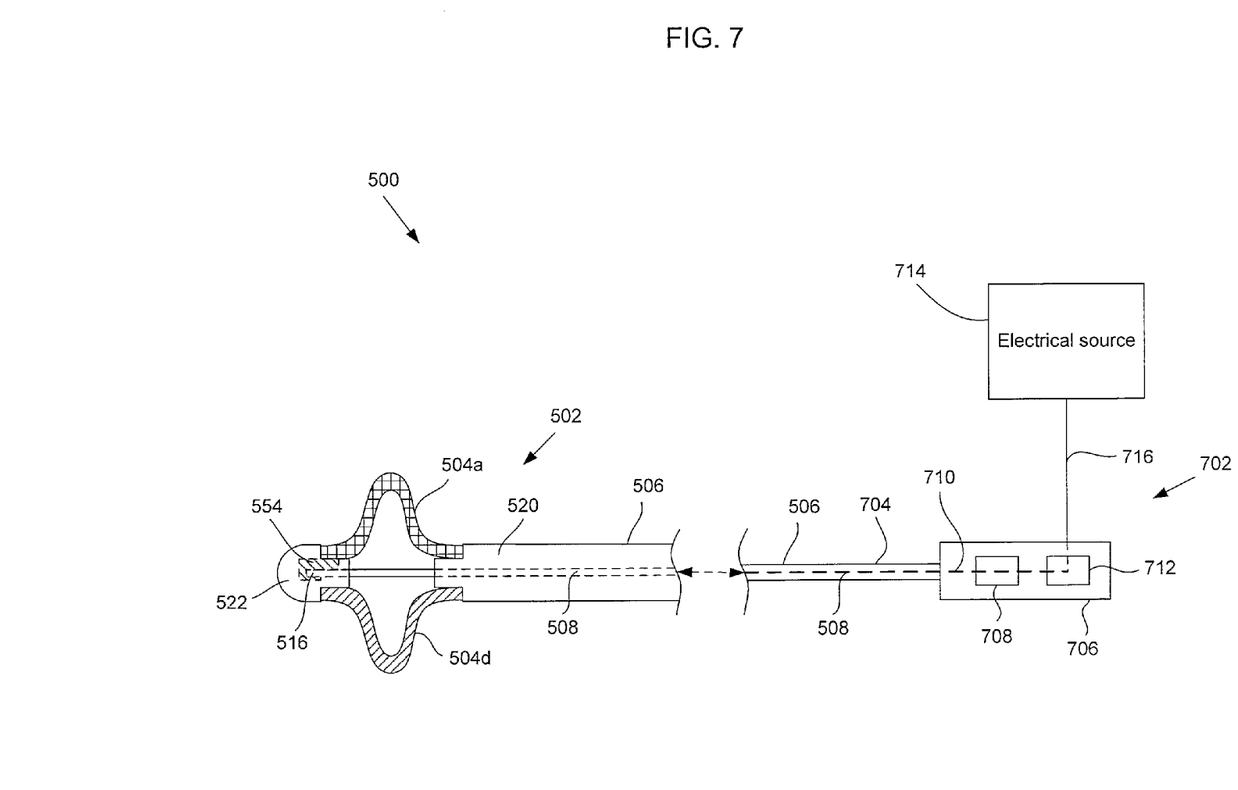
FIG. 7 shows a cross-section side view of the example sphincterotome shown in FIGS. 5 and 6, showing both the distal portion and a proximal portion of the sphincterotome.

The tines 504 may be part of an expandable basket such as the expandable basket 200 or the expandable basket 300 shown in FIGS. 2-4. For example, tines 504a and 504d may correspond to tines 304a and 304d, which are shown in cross-section in FIG. 4. The tines 504 may extend from a proximal end 514 to a distal end 512. Each of the proximal end 514 and the distal end 512 may be connected to and/or disposed on a portion of the tubular member 506. At the distal portion 502 of the sphincterotome 500, the tubular member 506 may include two portions, a proximal portion 520 and a distal portion 522. The proximal portion may be connected to one or more portions of the tubular member 506 proximal the distal portion 502 and extending to a proximal end of the sphincterotome, as shown in FIG. 7. The distal portion 522 may be physically separated from and/or physically unconnected with the proximal portion 520 and also the rest of the tubular member 506 proximal the distal portion 502 of the sphincterotome 100. A longitudinal length of the distal portion 522 may be configured to be as short as possible, and in one example configuration may be in a range of approximately one-tenth (0.1) inches to four-tenths (0.4) inches. The proximal portion 520 and the distal portion 522 may also be operably coupled to each other via a stylet 508 and/or the tines 504. The proximal portion 520 and the distal portion 522 may be configured to move axially relative to each other.

Each of the proximal portion 520 and the distal portion 522 may include a shoulder on or over which the ends 512, 524 of the tines 504 may be disposed. For example, the proximal portion 520 may include a shoulder 524, and the proximal end 514 of the tines 504 may be disposed on or over the shoulder 524. Similarly, the distal portion 522 may include a shoulder 526, and the distal end 512 of the tines 504 may be disposed on or over the shoulder 526. An inner diameter of the proximal end 514 may be greater than an outer diameter of the shoulder 524 so that the proximal end 514 may be moved over the shoulder 524. Similarly, an inner diameter of the distal end 512 may be greater than an outer diameter of the shoulder 526 so that the distal end 512 may be moved over the shoulder 526. In one example configuration, the outer diameters of the shoulders 524, 526 may be the same or substantially the same. In one example, an outer diameter of the ends 512, 514 may be twenty-eight one-thousandths (0.028) of an inch and an inner diameter of the ends 512, 514 may be seventeen one-thousandths (0.017) of an inch. Also, the outer diameters of the shoulders 524, 526 may each be sixteen one-thousandths (0.016) of an inch. Additionally, the shoulders 524, 526 may each be three-tenths (0.3) inches in length. Other dimensions may be used.

Outer surfaces of the shoulders 524, 526 may be adjacent and/or connected to side walls that function as stops and/or biasing points at which the tubular member 506 biases the tines 504 to move the tines 504 between the expanded and unexpanded configurations. For example, an outer surface 532 of the shoulder 524 may be adjacent and/or connected to a side wall 528, which functions as a stop and/or biasing point at which the tubular member 506 biases the tines 504 at the proximal end 514. Similarly, an outer surface 534 of the shoulder 526 may be adjacent and/or connected to a side wall 530, which functions as a stop and/or biasing point at which the tubular member 506 biases the tines 504 at the distal end 512. The side wall 528 may be perpendicular or substantially perpendicular to the outer surface 532. Also, the side wall 528 may be adjacent to an outer surface 536 of a portion 538 (referred to as a biasing portion) proximately adjacent and connected to the shoulder 524. The biasing portion 538 may have an outer diameter that is greater than the outer diameter of the shoulder 524. For example, the outer diameter at the biasing portion 538 may be twenty-seven one-thousandths (0.027) of an inch and the outer diameter of the shoulder 524 may be sixteen one-thousandths (0.016) of an inch, although other dimensions for the outer diameters may be used. The side wall 528 may function and/or serve as a bump-down or a step-down from the biasing portion 538 to the shoulder 524. Likewise, the sidewall 530 may be perpendicular or substantially perpendicular to the outer surface 534 of the shoulder 538. Also, the side wall 530 may be adjacent to an outer surface 540 of a portion 542 (referred to as a biasing portion) distally adjacent and connected to the shoulder 526. The biasing portion 542 may have an outer diameter that is greater than the outer diameter of the shoulder 526. For example, the outer diameter at the biasing portion 542 may be twenty-seven one-thousandths (0.027) of an inch and the outer diameter of the shoulder 526 may be sixteen one-thousandths (0.016) of an inch, although other dimensions for the outer diameters may be used. The side wall 530 may function and/or serve as a bump-down or step-down from the biasing portion 542 to the shoulder 526. In addition, the outer surface 540 may distally extend to a distal tip 544. As shown in FIG. 5, the distal tip 544 may be rounded to provide an atraumatic tip as the sphincterotome 500 is moved to and from a treatment site. In alternative configurations, one or both of the side walls 528, 530 may not be perpendicular, and instead by at an angle less than ninety degrees with respect to the outer surfaces 534, 536 so that transitions (e.g., the step-downs or bump downs) from the shoulders 524, 526 to the biasing portions 538, 542 is more gradual than where the side walls 528, 530 are perpendicular to the outer surfaces 534, 536.

When the ends 512, 514 of the tines 504 are disposed on or over the shoulders 530, 528, the ends 512, 514 may be disposed on the shoulders 530, 528 so that they abut and/or contact the side walls 530, 528. For example, the end 512 may abut and/or contact the side wall 530. Similarly, the end 514 may abut and/or contact the side wall 528. As explained in more detail, by abutting and/or contacting the ends 512, 514, the side walls 530, 528 may be configured to axially bias or unbias the ends 512, 514 to move the tines 504 to and from the expanded and unexpanded configurations.

As described above, the proximal portion 520 and the distal portion 522 may be operably coupled using the stylet 508. The stylet 508 may extend within the tubular member 506 from a proximal portion of the sphincterotome 500 (shown in FIG. 7) to the distal portion 502. The stylet 508 may extend within a central lumen of the tubular member 506. For example, as shown in FIG. 5, the stylet 508 extends through a central lumen 546 of the proximal portion 520. The central lumen may define an inner diameter of the proximal portion 520, which may be thirteen one-thousandths (0.013) of an inch, as an example. The stylet may have a thickness or a cross-sectional width that is less than the inner diameter of the proximal portion 520, such as eleven one-thousandths (0.011) of an inch, as an example. The stylet 508 may also extend within and/or through a central lumen of an expandable basket, such as the central lumen 230 of the expandable basket 200 shown in FIG. 2. The stylet 508 may further be fixedly attached to the distal portion 522. As shown in FIG. 5, a distal end 516 of the stylet 508 may be fixedly attached to an inner portion 550 of the distal portion 522. Various configurations may be used to fixedly attach the stylet 508 to the distal portion 522. For example, the distal end 516 and the inner portion 550 may each have a threaded configuration and threads of the distal end 516 may engage with threads of the inner portion 550. Alternatively, the distal end 516 may be soldered to the inner portion 550. In another alternative configuration, an adhesive or epoxy may be used to fixedly attach the distal end to the inner portion 550. Various other configurations may be used.

In one example configuration, as shown in FIG. 5, the stylet may extend through a central lumen 548 of the distal portion 522 before being fixedly attached at the inner portion 550. Like the central lumen 546 of the proximal portion 520, the central lumen 548 of the distal portion 522 may define an inner diameter of the distal portion 522, which may be thirteen one-thousands (0.013) of an inch, as an example. The central lumen 548 may be axially aligned or substantially axially aligned with the central lumen 546 of the proximal portion 520. Alternative configurations of the distal portion 522 may not include the central lumen 548. In other alternative configurations, the central lumen 548 may be part of and/or comprise the inner portion 550, and the stylet 508 may be fixedly attached to the distal portion 522 along all or a part of the central lumen. For example, the distal end 516 of the stylet 508 may have a threaded configuration that engages with a threaded configuration of the inner portion that extends an entire length of the lumen 548.

The stylet 508 may be movably disposed within the central lumen 546 and be configured to move axially relative to the proximal portion 520 within the central lumen 546. By being fixedly attached to the distal portion 522 and axially moving relative to the proximal portion, the stylet may be configured to axially move the distal portion 522 relative to the proximal portion 520. By axially moving the distal portion 522 relative to the proximal portion 520, the stylet may be configured to move the tines 504 between the expanded configuration and the non-expanded configuration. FIG. 5 shows the tines 504 in the non-expanded configuration. In the non-expanded configuration, the stylet 508 may position the distal portion 522 at a sufficient distance distally away from the proximal portion 520 so that the ends 512, 514 of the tines are disposed on or over the respective shoulders 534, 532, and also so that the ends 512, 514 are unbiased or substantially unbiased by the sidewalls 530, 528 so that the tines 504 are in a straightened or substantially straightened configuration.

Figure 6:
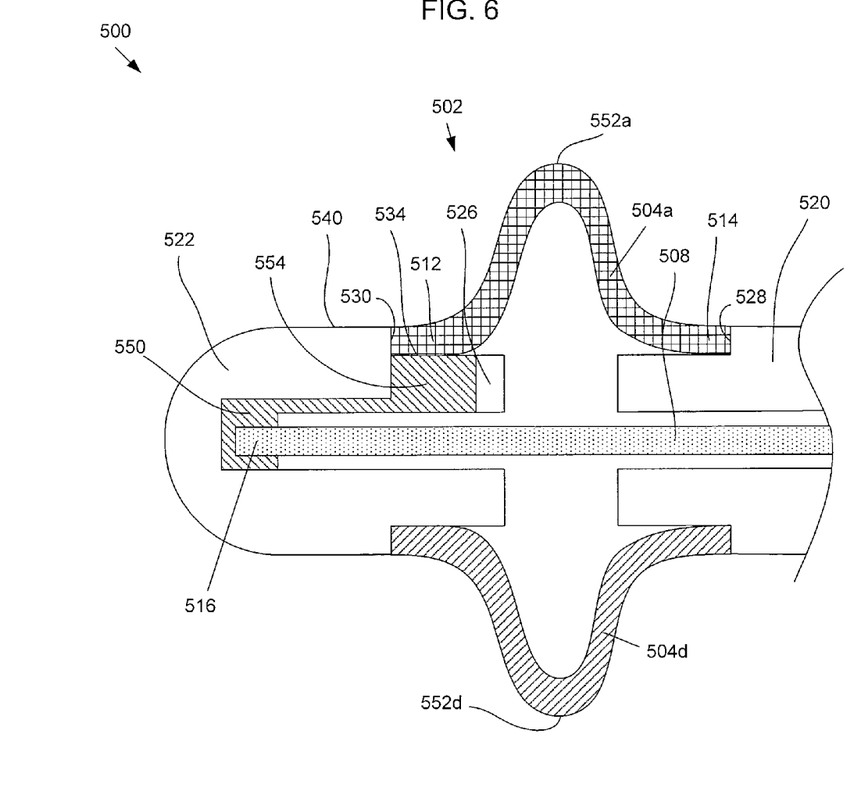
FIG. 6 shows a cross-sectional side view of the distal portion of the example sphincterotome shown in FIG. 5, where the tines are configured in the expanded configuration.

FIG. 6 shows the distal portion 502 of the sphincterotome 500 shown in FIG. 5, where the tines are configured in the expanded configuration. The stylet 508 may be configured to move the tines 504 from the non-expanded configuration to the expanded configuration by proximally moving the distal portion 522 relative to the proximal portion 520. As the stylet 508 proximally moves the distal portion 522 relative to the proximal portion 520, the side walls 528, 530 axially bias the ends 514, 512 in opposing directions. For example, the side wall 528 axially biases the end 514 in the distal direction, and the side wall 530 axially biases the end 512 in the proximal direction. In other words, as the stylet 508 moves the proximal and distal portions 520, 522 closer together, the proximal and distal portions 520, 522 are configured to axially compress the tines 504. When the tines 504 are axially compressed, the tines are configured to radially expand away from the tubular member 506 and move to the expanded configuration. As shown in FIG. 6, when the tines 504 are in the expanded configuration, the tines 504 may be in a curved, such as a bell-shaped curved, configuration. In the expanded configuration, outer-most portions 552 of the tines 504 may contact and/or outwardly bias and/or widen an opening of the sphincter muscle, which due to its constrictive nature, is trying to close. The tine that is the cutting wire 504 may be configured to cut the sphincter muscle at the outer-most portion 552a. The outer-most portions of the other tines—e.g., outer-most portion 552d of tine 504d shown in FIG. 6—may outwardly bias the opening of the sphincter muscle at portions of the sphincter muscle, other than the portion being cut, to stabilize the cutting wire 504a as the cutting wire 504a is cutting the sphincter muscle.

The stylet 508 may also distally move the distal portion 522 relative to the proximal portion 520 to move the tines 504 from the expanded configuration to the unexpanded configuration. That is, the stylet 508 may distally move the distal portion 522 away from the proximal portion 520 to axially decompress and/or remove their axial bias on the tines 504. As the stylet 508 distally the distal portion 522 relative to the proximal portion 520, the side wall 528 removes its axial bias on the end 514 and the side wall 530 removes its axial bias on the end 512. As the axial bias is removed, the ends 512, 514 may be configured to axially move along with the side walls 528, 530 and axially expand until the tines 504 are straightened or substantially straightened in the unexpanded configuration, as shown in FIG. 5.

The stylet 508 may further be configured to be electrically coupled to the cutting wire 504a and to provide an electrical signal, such as electric current, to the cutting wire 504a. As shown in FIG. 7, a proximal end of the stylet 508 may be electrically coupled to an electrical source that provides the electrical signal to the cutting wire 504a. The stylet 508 may be made of an electrically conductive material to transmit the electrical signal from the electrical source to the cutting wire 504a. To electrically couple the stylet 508 to the cutting wire 504a, the distal portion 522 may include a connector portion 554 that connects the stylet 508 to the cutting wire 504a. The connector portion may be made of an electrically conducting material, such as copper, gold, or solder paste as examples. In one example configuration as shown in FIGS. 5 and 6, the connector portion 554 is configured to electrically connect the distal end 516 of the stylet with the distal end 512 of the tines 504. The connector portion extends from the inner portion 550, where the stylet 508 is fixedly attached to the distal portion 522, to the outer surface 534 of the shoulder 526, where the end 512 is connected to the distal portion. Various other configurations for the connector portion 554 may be used to electrically connect the stylet 508 to the cutting wire 504a. Additionally, the connector portion 554 may be configured in the interior of the distal portion so that the outer surface 540 is electrically insulated from the stylet and/or the cutting wire 504a. Also, the connector portion 554 is configured to be unconnected with the other tines—e.g., tine 504d shown in FIGS. 5 and 6—that are configured as stabilizing wires so that the other tines are electrically insulated from the stylet 508 and the cutting wire 504a.

FIG. 7 shows a cross-sectional side view of the sphincterotome 500, showing both the distal end 502 and a proximal end 702 of the sphincterotome 500. At the proximal end 702, a proximal portion 704 of the tubular member 506 may be connected to a handle 706. An operator and/or physician may operate the sphincterotome 500 using the handle 706. The handle 706 may include a stylet-controlling device 708 that is operatively coupled to the stylet 508 and that is configured to axially move the stylet 508. The stylet 508 may connected to the stylet-controlling device 708 at a proximal end 710 of the stylet 508. Various configurations may be used to axially move the stylet 508. For example, the proximal end 710 of the stylet 508 may have a threaded configuration that engages with a threaded configuration of the stylet-controlling device 708. The stylet-controlling device 708 may be configured to axially move the stylet 508 by rotating the stylet 508 in either a clock-wise or counter-clock wise direction, depending on a desired direction of movement of the stylet 508 and the threaded configuration. Referring back to FIGS. 5 and 6, the ends 512 may not be fixedly attached to the shoulders 530. As such, when the stylet 508 is being rotated, causing the distal portion 522 to be rotated as well, the tines 504 are not also rotating along with the stylet 508 and the distal portion 522. Also, the end 512 may or may not be fixedly attached to the shoulder 528. In an alternative example configuration, the stylet-controlling device 708 may be configured to axially move the proximal end 710 of the stylet 508 to axially move the entire stylet 508. In the alternative configuration, the proximal end 710 of the stylet may be slidably connected to the stylet-controlling device 708. The stylet-controlling device 708 may include electronic control and/or mechanical control to axially move the stylet 508. The stylet-controlling device 708 may also include an electronic and/or mechanical monitoring device that is configured to track and/or determine how far the stylet is moved. The monitoring device may be used to prevent the distal portion 522 from being distally moved too far away from the proximal portion 520 and/or the distal portion 522 from being proximally moved too close to the proximal portion 520. In addition or alternatively to the monitoring device, the handle 706 may include one or more blocking devices that define and/or create an axial range in which the stylet 508 can be moved. The blocking devices may be resistant to any electrical or mechanical force applied to the stylet 508 that would cause the stylet 508 to move the distal portion 522 too far away from and/or too close to the proximal portion 520. The axial range may be a predetermined range established during assembly and/or manufacture of the handle 706.

In addition, the stylet-controlling device 708 may include a locking device, such as a thumb screw, that is configured to lock the stylet 508 in and release the stylet 508 from a locked position. For example, when the tines 504 are in the expanded configuration and/or the unexpanded configuration, the locking device 708 may be configured to lock the stylet 508 to prevent the stylet 508 from accidentally and/or undesirably moving the tines out of the expanded and unexpanded configurations. Also, before moving the tines from the expanded configuration to the unexpanded configuration, or vice versa, the lock on the stylet 508 set by the locking device may be released so that the stylet 508 may be axially moved.

The sphincterotome 500 may also include a connector 712 that electrically couples the stylet 508 to an electrical source 714. In one example, the electrical source 714 may be an electrosurgical unit (ESU). In addition, an example connector may include an electrocautery pin that connects the proximal end 710 of the stylet with an electrical connection 716 that transmits an electrical signal generated by the electrical source 714 to the handle 706. In one example configuration, the connector 712 may be a component of the handle 706, as shown in FIG. 7. In an alternative configuration, the connector 712 may be a component that is separate from the handle 706. Also, as shown in FIG. 7, the connector 712 may be a component that is separate from the stylet-controlling device 708. In one example, the proximal end 710 of the stylet 508 may extend through the stylet controlling device and a proximal tip of the stylet 508 is connected to the connector 712. In alternative configurations, the connector 712 may be a component of the stylet-controlling device 708 or the connector 712 may connect the stylet 508 to the electrical connector 708 before the proximal end 710 is connected to the stylet controlling device 708. Various configurations are possible.

The electrical source 714 may be configured to generate and/or provide an electrical signal, such as electric current, to the connector 712 via the electrical connection 716 connecting the electrical source 714 to the connector 712. In turn, the connector 712 provides the electrical signal to the proximal end 710 of the stylet 508. The stylet 508 is configured to transmit the electrical signal toward the distal end 516, where the stylet 508 is fixedly attached to the distal portion 522 of the tubular member 506. The electrical signal is transmitted from the distal end 516 of the stylet 508, through the connector portion 554 of the distal portion, to the cutting wire 504a.

The distal portion 502 of the sphincterotome may be assembled in various ways. In one example, the stylet 508 may be connected to the handle 706 and distally advanced through a central lumen of the tubular member, including the central lumen 546 of the proximal portion 520, where the distal end 516 of the stylet 508 distally protrudes from the proximal portion 520. The tines 504, which may be configured as an expandable basket, may proximally inserted over the distal end 516 of the stylet and the shoulder 524 until the proximal end 514 of the tines 504 abuts and/or comes into contact with the side wall 528. The distal end 516 of the stylet 508 may then be fixedly attached to the distal portion 522. The distal portion 522 may then be proximally advanced so that the shoulder 526 of the distal portion 522 is inserted in the central lumen of the expandable basket so that the end 512 is disposed over the shoulder 526. The distal portion 522 may be proximally advanced, at least in part, by proximally moving the proximal end 710 of the stylet 508 using the handle 706. The distal portion 522 may be proximally advanced until the end 512 abuts and/or comes into contact with the side wall 530.

Figure 8A:
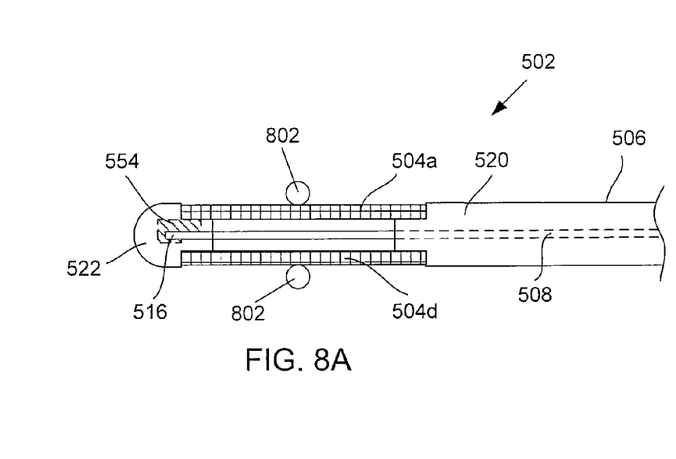
FIG. 8A shows a cross-sectional side view of the distal portion of the sphincterotome of FIG. 5 in the non-expanded configuration inserted through an opening of a sphincter muscle.
Figure 8B:
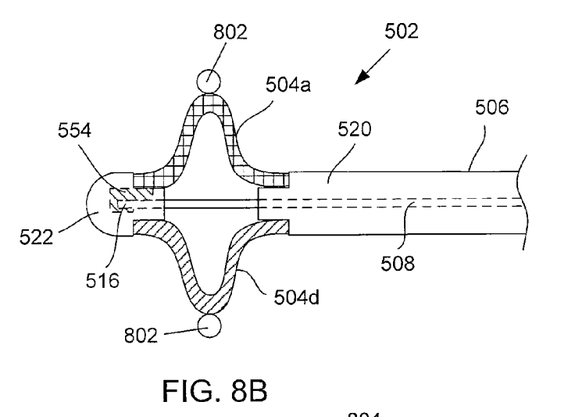
FIG. 8B shows a cross-sectional side view of the distal portion of the sphincterotome of FIG. 5 in the expanded configuration, having expanded the opening of the sphincter muscle.
Figure 9A:
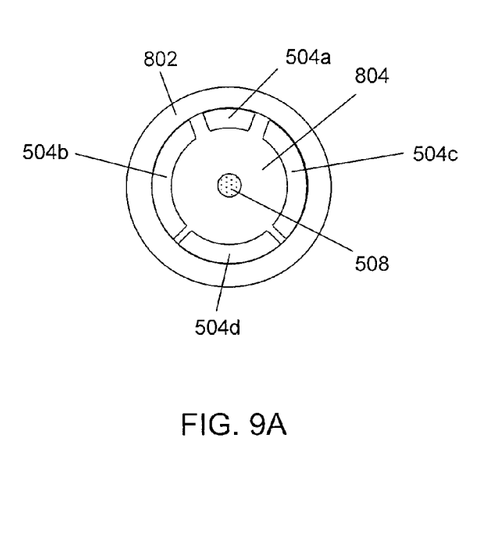
FIG. 9A shows an axial view of the distal portion of the sphincterotome of FIG. 5 in the non-expanded configuration, shown in cross-section at the position where the sphincter muscle is contracted around the tines.
Figure 9B:
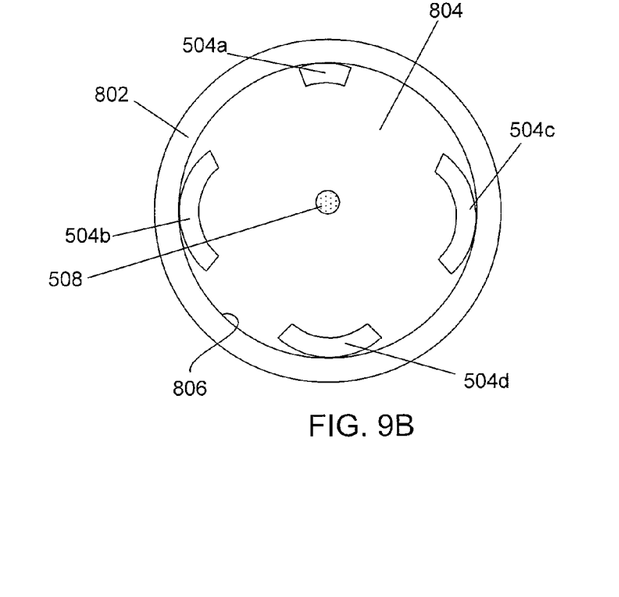
FIG. 9B shows an axial view of the distal portion of the sphincterotome of FIG. 5 in the expanded position, shown in cross-section at the position where the opening of the sphincter muscle is being expanded by the tines.

The following description now describes an example operation of the sphincterotome 500 with reference to FIGS. 8A, 8B, 9A, 9B. FIG. 8A shows a cross-sectional side view of the distal portion 502 sphincterotome 500 in the non-expanded configuration inserted through an opening of a sphincter muscle 802. FIG. 8B shows a cross-sectional side view of the sphincterotome 500 in the expanded configuration, having expanded the opening of the sphincterotome. FIG. 9A corresponds to FIG. 8A and shows an axial view of the distal portion 502 of the sphincterotome 500 in the non-expanded configuration, shown in cross-section at the position where the sphincter muscle 802 is contracted around the tines 504. FIG. 9B corresponds to FIG. 8B and shows an axial view of the distal portion 502 of the sphincterotome 500 in the expanded position, shown in cross-section at the position where the opening 804 of the sphincter muscle 802 is being expanded by the tines 504.

In an initial configuration, shown in FIGS. 8A and 9A, the tines 504 may be configured in the non-expanded configuration. If not already in the non-expanded configuration, the stylet-controlling device 708 of the handle 706 (shown in FIG. 7) may be operated to distally move the distal portion 522 relative to the proximal portion 520 until the tines are substantially straightened in the non-expanded configuration and/or until the blocking mechanism of the handle 706 prevents the stylet 508 from being further distally moved. Also, any locking mechanisms in the handle may be activated to lock the tines 504 in the non-expanded configuration. The tubular member 506, beginning with the distal portion 522, may then be inserted into a patient and distally advanced toward the sphincter muscle 802 to perform electrocautery.

Shown in FIGS. 8A and 9A, the distal portion 502 may be distally advanced through the constrictive opening 804 of the sphincter muscle until the sphincter muscle 802 surrounds or is contracted around a desired point of the tines 504. The desired point of the tines 504 may be a midpoint, which may also be the outer-most point of the tines 504 when the tines 504 are in the expanded configuration. The distal portion 502 may also be rotated if necessary so that the tine configured as the cutting wire 504a is positioned in a predetermined and/or desired cutting position. The cutting position may be a vertical or twelve o'clock position. An indicator, such as the indicator 120 shown in FIG. 1, may be used to identify which of the tines 504 is the cutting wire 504a when moving the cutting wire 504a in the cutting position and which of the tines 504 are the stabilizing wires 504b, 504c, 504d.

In the cutting position, the stylet 508 may be proximally moved to move the distal portion 522 toward the proximal portion 520, as shown in FIG. 5B. Where the handle 706 includes a locking mechanism to lock the stylet 508, the locking mechanism may first be unlocked so that the stylet 508 can be moved. When the distal portion 522 is proximally moved relative to the proximal portion 520 using the stylet 508, the side walls 528, 530 axially compress the tines 504 so that the tines 504 move to the expanded configuration. In doing so, the tines radially and outwardly bias the inner wall 806 of the sphincter muscle 802, which widens the opening 804 of the sphincter muscle 802, as shown in FIGS. 8B and 9B. As the tines 504 are being moved, the distal portion 502 may be distally or proximally moved as is necessary. In the expanded configuration, the tines 504 may form a curved shape, such as a bell-shaped curve, and outer-most portions of the tines 504 may bias the inner wall 806 of the sphincter muscle 802. Also, in the expanded configuration, the locking mechanism may be activated to prevent axial movement of the stylet 508 and lock the tines 508 in the expanded configuration.

When the tines 504 are moved to the expanded configuration, the electrical source 714 may be activated to output an electrical signal. The electrical signal may be sent to the stylet 508 via the electrical connection 716 and the connector 712. The electrical signal is transmitted distally down the stylet 508 to the distal end 516. The electrical signal passes through the connector portion 554 and to the cutting wire 504a. When electrically activated, the cutting wire 504a may cut the sphincter muscle 802, relaxing the constrictive nature of the muscle. As the cutting wire 504a cuts the sphincter muscle 802, the other tines configured as stabilizing wires 504b, 504c, 504d stabilize the cutting wire 504a in the cutting position and/or maintain the sphincter muscle 802 in a widened position. The radial expansion of the tines 504 may be increased or decreased through axial movement of the stylet 508 while the cutting wire 504a is cutting, as deemed necessary.

When the cutting wire 504a is finished cutting the sphincter muscle 802, the electrical source 714 may be deactivated, which stops the flow of electric current to the cutting wire 504a. Then, the tines 504 may be radially retracted and/or moved to the non-expanded configuration by distally moving the stylet 508. The locking mechanism may first be unlocked to allow for the movement. When the tines 504 are in the non-expanded configuration, tubular member 506, including the distal portion 502, may be distally moved away and/or retracted from the sphincter muscle 802 and out of the patient.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

I claim:

1. A sphincterotome comprising:
   a plurality of tines longitudinally disposed at a distal portion of the sphincterotome, the plurality of tines movable between an expanded configuration and a non-expanded configuration,
   wherein only one of the tines is a cutting wire that is configured to be electrically coupled to an electrical source,
   wherein the other of the tines are stabilizing wires and are electrically insulated from the cutting wire, and
   wherein each of the plurality of tines, including the one that is the cutting wire, forms a curve in the expanded configuration.

2. The sphincterotome of claim 1, further comprising a stylet that is operatively coupled to the plurality of tines, wherein axial movement of the stylet moves the plurality of tines between the expanded configuration and the non-expanded configuration.

3. The sphincterotome of claim 2, wherein the plurality of tines are configured as an expandable basket.

4. The sphincterotome of claim 3, wherein the stylet is operatively coupled to a distal end of the basket, wherein the stylet axially moves relative to a proximal end of the basket to expand and contract the basket.

5. The sphincterotome of claim 3, wherein the expandable basket comprises:
a tubular member having a plurality of slots longitudinally extending through a wall of the tubular member to define the tines,
wherein each of the plurality of tines are formed by two of the plurality of slots.

6. The sphincterotome of claim 5, wherein the tubular member is configured to axially compress and decompress, and
wherein the tines are configured to radially expand when the tubular member is being compressed and radially retract when the tubular member is being decompressed.

7. The sphincterotome of claim 2, further comprising an elongate tubular member having a distal end comprising:
a proximal portion; and
a distal portion that is distal and axially aligned with the proximal portion;
wherein the stylet longitudinally extends through a central lumen of the proximal portion and is movably disposed therein,
wherein the stylet is fixedly attached to the distal portion, and
wherein the stylet is configured to axially move the distal portion relative to the proximal portion to move the plurality of tines between the expanded configuration and the non-expanded configuration.

8. The sphincterotome of claim 7, wherein each of the proximal portion and the distal portion comprises a shoulder, and
wherein a proximal end of the plurality of tines is disposed over the shoulder of the proximal portion and a distal end of the plurality of tines is disposed over the shoulder of the distal portion.

9. The sphincterotome of claim 8, wherein each of the proximal portion and the distal portion comprises a side wall,
wherein the side walls are configured to axially bias the proximal end and the distal end of the plurality of tines in opposing directions to move the tines between the expanded configuration and the non-expanded configuration.

10. The sphincterotome of claim 8, wherein the distal end of the plurality of tines is movably attached to the shoulder of the distal portion.

11. The sphincterotome of claim 7, wherein stylet is electrically coupled to the cutting wire, the stylet being configured to deliver electrical current to the cutting wire.

12. The sphincterotome of claim 10, wherein the distal portion comprises a connector portion that electrically connects the stylet to the cutting wire.

13. The sphincterotome of claim 11, wherein the connector portion comprises an internal part of the distal portion, and wherein an outer surface of the distal portion is electrically insulated from the connector portion.

14. The sphincterotome of claim 7, wherein the distal portion comprises an atraumatic tip disposed at a distal end of the distal member.

15. The sphincterotome of claim 1, wherein the curve comprises a bell-shaped curve.

* * * * *